United States Patent [19]

Biedermann

[11] Patent Number: 5,676,640

[45] Date of Patent: Oct. 14, 1997

[54] ORTHESIS JOINT SYSTEM

[75] Inventor: Lutz Biedermann, VS-Villingen, Germany

[73] Assignee: Biedermann Motech GmbH, VS-Schwenningen, Germany

[21] Appl. No.: 622,667

[22] Filed: Mar. 26, 1996

[30] Foreign Application Priority Data

Jul. 4, 1995 [DE] Germany .................. 195 13 268.8

[51] Int. Cl.⁶ .................................................. A61F 5/00
[52] U.S. Cl. .................................................. 602/26; 602/16
[58] Field of Search ................................ 602/5, 16, 23, 602/26

[56] References Cited

U.S. PATENT DOCUMENTS

| | | |
|---|---|---|
| 2,943,622 | 7/1960 | Nelson . |
| 4,340,041 | 7/1982 | Frank ........................... 602/16 |
| 4,370,977 | 2/1983 | Mauldin et al. ............... 602/16 |
| 4,493,316 | 1/1985 | Reed et al. . |
| 4,506,661 | 3/1985 | Foster . |
| 4,643,176 | 2/1987 | Mason et al. ................. 602/16 |
| 5,036,837 | 8/1991 | Mitchell et al. . |
| 5,062,858 | 11/1991 | Broeck et al. . |
| 5,292,303 | 3/1994 | Bastyr et al. . |

FOREIGN PATENT DOCUMENTS

679910 A5   5/1992   France .

Primary Examiner—Linda C. Dvorak
Attorney, Agent, or Firm—George W. Neuner

[57] ABSTRACT

A system for a mono-axial and a duo-axial orthesis joint is created. The system comprises a first and a second post (1, 2), a mono-axial cover (21) and two duo-axial covers (3). The posts (1, 2) each have a shaft bore (4, 5) at a first end thereof and toothed portions (6, 7) provided at the first ends of the posts (1, 2). One shaft bore (22) is provided in the mono-axial cover and two spaced shaft bores (3, 4) are provided in the duo-axial cover (3). The distance between the shaft bores is so that in the duo-axial construction both toothed portions (6, 7) engaged each other.

15 Claims, 3 Drawing Sheets

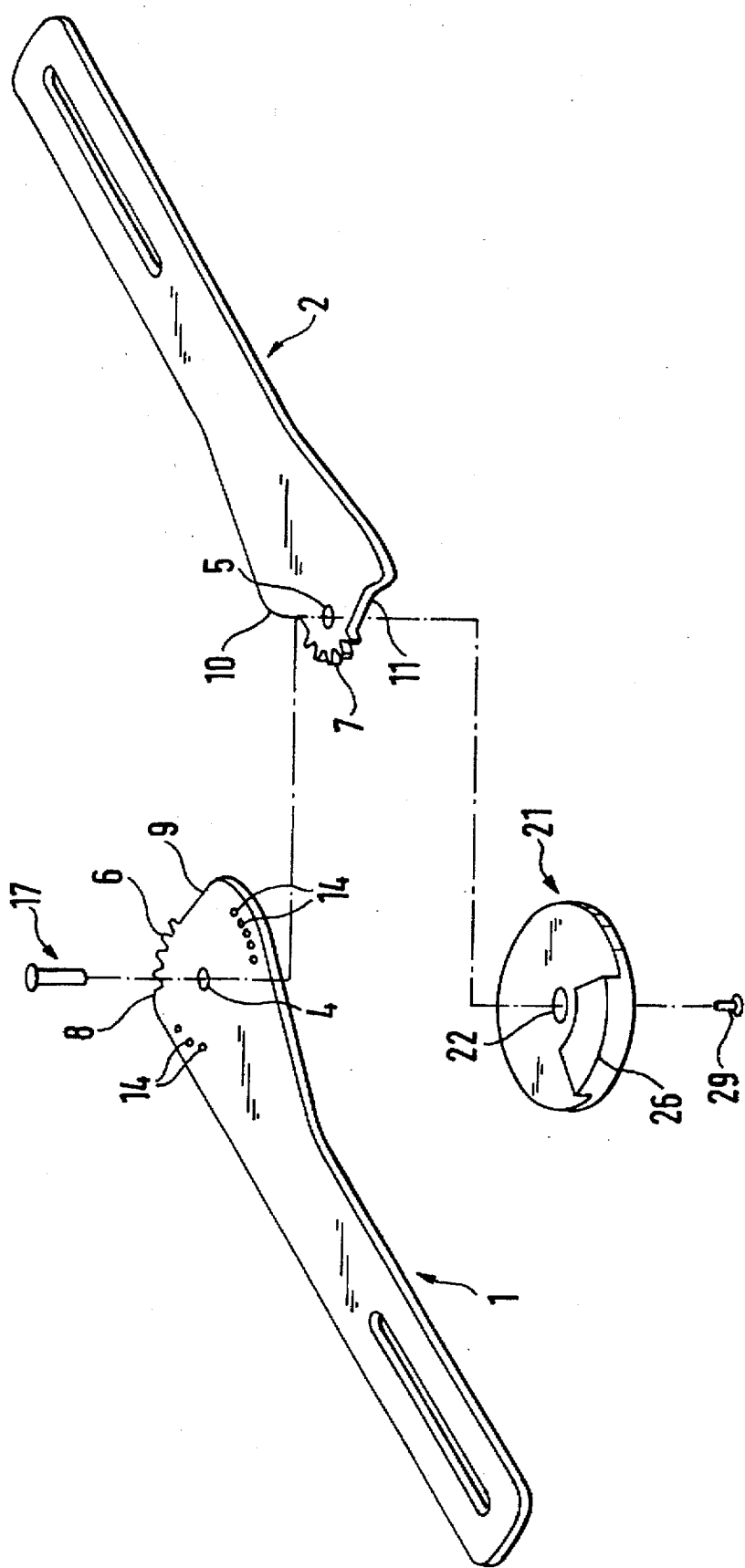

ORTHESIS JOINT SYSTEM

The invention relates to an orthesis joint system.

There are orthesis joints having either one axis or two axes. The U.S. Pat. No. 4,493,316 discloses a duo-axial orthesis joint hingedly connecting a thigh part with a lower leg part. The components for a mono-axial orthesis joint as well as the components for a duo-xial orthesis joint must be produced and stored separately from each other.

It is the object of the invention to provide a system allowing the production of mono-axial as well as duo-axial orthesis joints using the smallest possible number of components.

This object is achieved by the system defined in claim 1.

Further embodiments of the invention are defined in the subclaims.

Embodiments of the invention are described with reference to the figures. In the figures:

FIG. 4 is an exploded representation of a mono-axial embodiment of a knee orthesis joint of the system.

Figure 1:
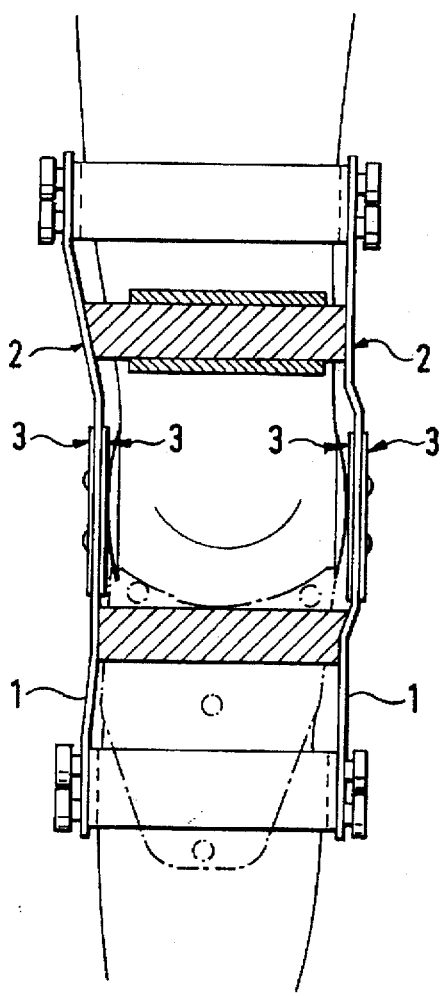
FIG. 1 shows a knee orthesis having a duo-axial joint.
Figure 2:
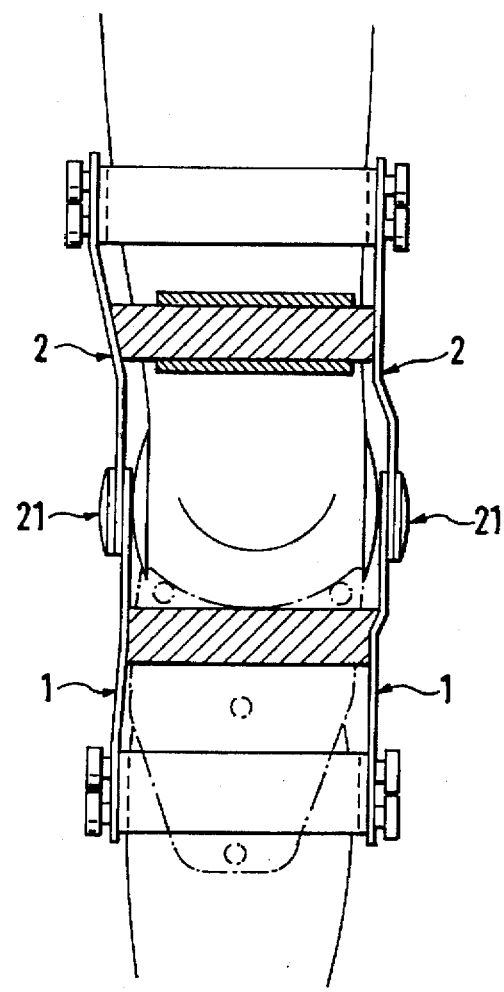
FIG. 2 shows a knee orthesis with a mono-axial joint.
Figure 3:
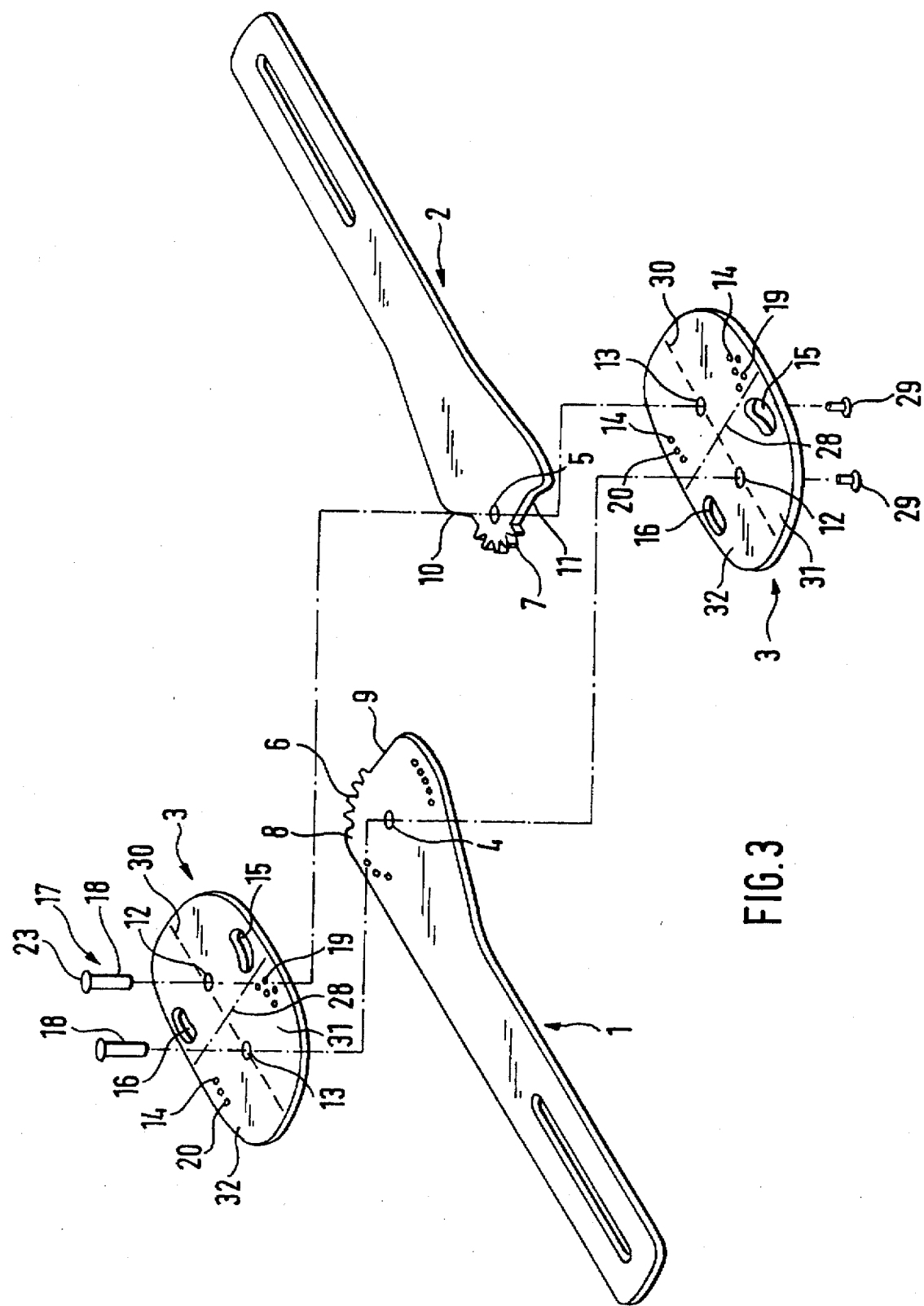
FIG. 3 is an exploded representation of a duo-axial embodiment of the knee orthesis joint of the system.

According to a first embodiment the system consists of a first post 1, a second post 2, two duo-axial covers 3 and a mono-axial cover 21.

For making a duo-axial knee orthesis joint the first post 1 and the second post 2 are hingedly connected by means of two duo-axial covers 3.

For making a mono-axial knee orthesis joint the first 1 and the second post 2 are hingedly interconnected by means of the mono-axial cover 21.

The first post 1 and the second post both have a shaft bore 4, 5 close to a first end thereof. Furthermore, both posts have a respective toothed portion 6, 7 at the first end. Respective cam paths 8, 9, 10, 11 are provided adjacent to each side of the toothed portions 6, 7. The first post 1 has, in a region adjacent to each cam path 8, 9, a plurality of threaded bores 14 which are spaced from each other and located on an arc of a circle having a predetermined diameter around the shaft bore 4.

The duo-axial cover 3 has an outer contour which is symmetric with respect to a center axis 28 lying in the plane of the cover. Two spaced bores 12, 13 are provided in the duo-axial cover 3 symmetric with respect to the center axis 28. The line connecting the bores 12, 13 crosses the center axis 28 and divides the same into two portions of substantially equal length. The distance between the bores 12, 13 is selected to provide for a mutual engagement of the two toothed portions 6, 7 in a duo-axial assembly. The connection line 30 of the bores 12, 13 divides the duo-axial cover into a first portion 31 and a second portion 32. The first portion 31 has a first region 19 of threaded bores 14 with a first outer contour provided therein spaced from the bore 13 and the second portion 32 has a second region 20 of threaded bores 14 with a second outer contour provided therein spaced from the bore 13. The duo-axial cover 3 has a first hole 15 which is symmetric to the first region 19 with respect to the center axis 28 and has an outer contour which is greater than that of the first region 19, and a second hole 16 which is symmetric to the second region 20 with respect to the center axis and has an outer contour which is greater than that of the second region.

The mono-axial cover 21 has a circular outer contour with a radius and a coaxial bore 22 provided therein. A boss 26 has a height which substantially corresponds to the dimension of the second post 2 measured in axial direction of the shaft bore 5. The boss 26 is shaped as an angular circle with an outer radius corresponding to the radius of the mono-axial cover 21. Further, the boss 26 is arranged on the mono-axial cover 21 so that a center of the circular arc-shaped boss 26 coincides with a center of the mono-axial cover. The inner radius of the circular arc-shaped boss is greater than the greatest distance between a center of the bore 5 of the second post 2 and the toothed portion 7 of the post 2. The extension of the circular arc-shaped boss 26 in circular direction of the mono-axial cover is smaller than the smallest distance between the threaded bores 14 adjacent the one cam path 8 of the first post 1 and the threaded bores 14 adjacent to the other cam path 9 of the first post 1 measured in this circumferential direction.

Connection sleeves 17 and counterparts 29 are provided for connecting the posts and the covers. A connection sleeve 17 consists of a hollow cylinder 18 having an outer diameter which is sized in relation to the diameter of the bores 12, 13 so that it just fits and may rotate therein. A head 23 is provided at one end of the hollow cylinder in a longitudinal direction thereof. The mating counterpart 29 comprises a pin-shaped solid cylinder with a head provided at one end thereof in longitudinal direction of the solid cylinder. The outer diameter of the solid cylinder is selected so that the counterpart 29 is connected with the connection sleeve 17 by force fit when pushed into the same.

Moreover, stop pins P are provided. The stop pins P have an external screw thread at one end thereof. The external screw thread fits internal screw threads within the threaded bores 14. Preferably, a rubber ring is provided at the other end of the stop pins.

When assembling a duo-axial embodiment the first post 1 and the second post 2 are placed onto a first duo-axial cover 3 so that the shaft bore 5 of the second post 2 is aligned with the bore 13 of the duo-axial cover 3 and the shaft bore 4 of the first post 1 is aligned with the bore 12 of the first duo-axial cover 3, and that the toothed portions 6, 7 of the posts 1, 2 engage each other. Thereafter, a second duo-axial cover 3 is placed onto the posts in a position rotated by 180° around the center axis with respect to the first duo-axial cover 3 so that the bore 13 is aligned with the shaft bore 4 and the bore 12 is aligned with the shaft bore 5. Thereupon two connection sleeves 17 are pushed into the shaft bores 13, 4, 12; 12, 5, 13 from one side and the counterparts 29 are inserted into the connection sleeves 17 from the other side. A respective stop pin P is then screwed into one of the threaded bores 14 of the first region 19 and of the second region 20 through the holes 15, 16.

In operation a first angular end position of the orthesis joint is defined by bringing the cam path 8 and/or 10 into abutment with the stop pin provided in the second region 20. The second angular end position of the orthesis joint is defined by bringing the cam path 9 and/or 11 into abutment with the stop pin provided in the first region 19. Both angular end positions of the posts 1, 2 define a minimum angle between the posts 1, 2, i.e. the flexion limit of the orthesis joint, and a maximum angle between the posts 1, 2 i.e. the extension limit of the orthesis joint. Thus, the allowed angle range of the posts 1, 2 is adjusted.

Before assembling the mono-axial embodiment of the orthesis joint the angular range for the joint is defined by screwing a first stop pin into one of the threaded bores 14 adjacent to the cam path 8 and a second stop pin into one of the threaded bores 14 of the first post 1 adjacent to the cam path 9. Then the second post 2 is placed onto the mono-axial cover 21 whereby the shaft bores 5 and 22 aligned. Thereupon the first post 1 is placed onto the second post 2 and the shaft bores 4 and 5 are aligned. Thereafter, the connecetion sleeve 17 is pushed into the shaft bores from one side and the counterpart 29 is inserted into the connection sleeve from the other side, whereby the mono-axial knee orthesis joint is completed. Care must taken that the second cover 21 is arranged so that the boss 26 is placed over the first post 1. This improves the mechanical stability of the knee orthesis joint. The first angular end position of the orthesis joint results from the cam path 10 abutting the first stop pin. The second angular end position results from the cam path 11 abutting the second stop pin.

The posts 1, 2 and the assigned covers 3, 21 are made of a thermoplastic resin with or without fiber reinforcement such as glass fibers, carbon fibers or aramite fibers, or from light metals and alloys thereof such as titanium and aluminum. It is essential that these materials have a high inherent stability, corrosion resistance and low weight and that they can be postformed.

According to a further embodiment of the system only one duo-axial cover 3 is used for the duo-axial construction of the orthesis joint.

What is claimed is:

1. An orthesis joint system for constructing a mono-axial orthesis joint or a duo-axial orthesis joint, the system comprising:

a first post having two ends and a first shaft bore and a first toothed portion at one of said ends, a second post having two ends and a second shaft bore and a second post having two ends and a second shaft bore and a second toothed portion at one of said ends, a duo-axial cover means for constructing a duo-axial joint using said duo-axial cover means and said first and second posts, said duo-axial cover means comprising a third shaft bore and a fourth shaft bore, a first shaft extending through said third shaft bore and said first shaft bore for hingedly connecting said first post with said duo-axial cover means, and a second shaft extending through said fourth shaft bore and said second shaft bore for hingedly connecting said second post with said duo-axial cover means to assemble said duo-axial joint, said third shaft bore being spaced from the said fourth shaft bore for engagement of said first toothed portion with said second toothed portion in said assembled state, a mono-axial cover means alteratively engageable with said first and second posts, in lieu of said duo-axial cover means, for constructing a mono-axial joint using said mono-axial cover means and said first and second posts, a fifth shaft bore formed in said mono-axial cover means, and a third shaft extending through said fifth shaft bore and said first and second shaft bores for hingedly connecting said first and second posts to said mono-axial cover means.

2. The system of claim 1, wherein said duo-axial cover means further comprises a plurality of sixth bores for receiving a stop therein.

3. The system of claim 2, wherein said sixth bores are formed as threaded bores and the stop comprises a stop pin that can be screwed into one of the threaded bores in said duo-axial cover means.

4. The system of claim 2, wherein said stop comprises a stop pin that frictionally fits into one of said sixth bores in said duo-axial cover means.

5. The system of claim 2, further comprising a cam path formed at said first post adjacent to said first toothed portion for engagement with said stop.

6. The system of claim 1, wherein said first or said second post further comprises a plurality of seventh bores for receiving a stop therein.

7. The system of claim 6, wherein said seventh bores are formed as threaded bores and said stop comprises a stop pin that can be screwed into one of said threaded bores in said first or second post.

8. The system of claim 6, wherein said stop comprises a stop pin that frictionally fits into one of said seventh bores in said first or second post.

9. The system of claim 6, comprising a cam path formed at said first post adjacent to said first toothed portion for engagement with said stop.

10. The system of claim 1, further comprising a second duo-axial cover means for cooperating with said duo-axial cover means for hingedly interconnecting said first and second posts, both duo-axial cover means being perpendicular to the longitudinal axis of said first and second shaft bores, one duo-axial cover means being positioned on either side of said first and second posts.

11. The system of claim 10, wherein said duo-axial cover means comprises a connection axis extending through the centers of said third and fourth shaft bores, a first region formed close to said fourth shaft bore, said first region having a plurality of seventh bores for receiving a stop, and a second region having a hole which has a size slightly larger than said first region and which is located symmetrically to said first region with respect to said connection axis.

12. The system of claim 10, wherein said duo-axial cover means comprises a connection axis extending through the centers of said third and fourth shaft bores, a first region formed close to said fourth shaft bore, said first region having a plurality of seventh bores for receiving a stop, and a second region having a hole which has a size slightly larger than said first region and which is located symmetrically to said first region with respect to a center point between said third and fourth shaft bores at said connection axis.

13. The system of claim 10, wherein said duo-axial cover means comprises a connection axis extending through the centers of said third and fourth shaft bores, a first region formed close to said fourth shaft bore, said first region having a plurality of seventh bores for receiving a stop, and a second region having a hole which has a size slightly larger than said first region and which is located symmetrically to said first region with respect to a center axis lying in the plane of the surface of the duo-axial cover means, extending perpendicular to said connection axis and intersecting said connecting axis at the center point between said third and fourth shaft bores at said connection axis.

14. The system of claim 13, wherein said duo-axial cover means comprises a third region formed close to the fourth shaft bore and opposite to said first region, said third region having a plurality of eighth bores for receiving a stop, and a fourth region having a hole which has a size slightly larger than said third region and which is located symmetrically to said third region with respect to said connection axis.

15. The system of claim 1, further comprising a boss formed on said mono-axial cover means, said boss having a height corresponding to about the thickness of one of said posts when measured in the longitudinal direction of said first or second shaft bores.

\* \* \* \* \*

UNITED STATES PATENT AND TRADEMARK OFFICE
CERTIFICATE OF CORRECTION

PATENT NO. : 5,676,640
DATED : October 14, 1997
INVENTOR(S) : Lutz Biedermann

It is certified that error appears in the above-identified patent and that said Letters Patent is hereby corrected as shown below:

On the title page: Item [30] Foreign Application Priority Data:
" July 4, 1995" should read -- April 7, 1995--.

Signed and Sealed this

Ninth Day of December, 1997

Attest:

BRUCE LEHMAN

Attesting Officer

Commissioner of Patents and Trademarks